United States Patent
Sievert

(10) Patent No.: US 9,248,284 B2
(45) Date of Patent: Feb. 2, 2016

(54) SACRAL NEUROMODULATOR

(75) Inventor: Karl-Dietrich Sievert, Reutlingen (DE)

(73) Assignee: Karl-Dietrich Sievert, Reutlingen (DE)

( * ) Notice: Subject to any disclaimer, the term of this patent is extended or adjusted under 35 U.S.C. 154(b) by 0 days.

(21) Appl. No.: 13/415,166

(22) Filed: Mar. 8, 2012

(65) Prior Publication Data

US 2012/0221015 A1    Aug. 30, 2012

Related U.S. Application Data

(63) Continuation of application No. PCT/DE2010/001000, filed on Aug. 30, 2010.

(30) Foreign Application Priority Data

Sep. 11, 2009    (DE) .................. 10 2009 040 963

(51) Int. Cl.
*A61N 1/05* (2006.01)
*A61N 1/36* (2006.01)
*A61B 17/34* (2006.01)
*A61N 1/39* (2006.01)

(52) U.S. Cl.
CPC .............. *A61N 1/36007* (2013.01); *A61N 1/05* (2013.01); *A61B 17/3468* (2013.01); *A61N 1/3968* (2013.01)

(58) Field of Classification Search
CPC  A61N 1/0551; A61N 1/3408; A61N 1/36007
USPC ............................................. 607/40–41, 117
See application file for complete search history.

(56) References Cited

U.S. PATENT DOCUMENTS

| | | |
|---|---|---|
| 6,041,258 A | 3/2000 | Cigaina et al. |
| 6,165,180 A | 12/2000 | Cigaina et al. |
| 6,999,819 B2 | 2/2006 | Swoyer et al. |
| 2003/0045919 A1* | 3/2003 | Swoyer et al. ............... 607/122 |
| 2003/0233126 A1 | 12/2003 | Kaplan et al. |
| 2004/0210245 A1 | 10/2004 | Erickson et al. |
| 2004/0230279 A1* | 11/2004 | Cates et al. ................... 607/126 |
| 2005/0010260 A1* | 1/2005 | Gerber ............................ 607/39 |
| 2005/0143783 A1* | 6/2005 | Boveja et al. .................. 607/40 |
| 2006/0004421 A1 | 1/2006 | Bennett et al. |

(Continued)

FOREIGN PATENT DOCUMENTS

| | | |
|---|---|---|
| DE | 698 25 588 T2 | 1/2005 |
| GB | 2 048 682 A | 12/1980 |

OTHER PUBLICATIONS

European Search Report, European Patent Application No. 10 779 204.6, dated Mar. 12, 2013 (6 pages).

*Primary Examiner* — Carl H Layno
*Assistant Examiner* — Jennifer Ghand
(74) *Attorney, Agent, or Firm* — Burr & Brown, PLLC

(57) ABSTRACT

A stimulation electrode for a stimulation device for stimulating organs in the case of spinal paraplegia, more particularly in the case of detrusor sphincter dyssynergia, including an electrode shaft, at one end of which an electrode tip is arranged for emitting a stimulation signal and at the other end of which a connection region is provided for a signal line, and also at least one fixing mechanism for fixing the position of the electrode shaft in the surrounding tissue along the longitudinal axis of the electrode shaft, the fixing mechanism having at least one holding member preventing a withdrawal and at least one holding member preventing an advance.

18 Claims, 4 Drawing Sheets

(56) References Cited

U.S. PATENT DOCUMENTS

| | | |
|---|---|---|
| 2006/0190047 A1 | 8/2006 | Gerber et al. |
| 2007/0100411 A1 | 5/2007 | Bonde |
| 2007/0173900 A1* | 7/2007 | Siegel et al. .................... 607/41 |
| 2008/0103534 A1* | 5/2008 | Gerber .............................. 607/2 |
| 2008/0132970 A1 | 6/2008 | Barolat |
| 2009/0012592 A1 | 1/2009 | Buysman et al. |
| 2010/0131036 A1* | 5/2010 | Geistert et al. ................ 607/116 |

* cited by examiner

SACRAL NEUROMODULATOR

CROSS REFERENCE TO RELATED APPLICATIONS

This application is a continuation of International Application No. PCT/DE2010/001000 filed Aug. 30, 2010, which designated the United States, and claims the benefit under 35 USC §119(a)-(d) of German Application No. 10 2009 040 963.7 filed Sep. 11, 2009, the entireties of which are incorporated herein by reference.

FIELD OF THE INVENTION

The subject matter of the invention relates to a stimulation device with at least one stimulation electrode (unilateral) or stimulation electrodes (bilateral), and also to an insertion aid for a stimulation electrode and a method for stimulating organs.

BACKGROUND OF THE INVENTION

Micturition, defecation and sexual dysfunctions result from damage to the central autonomic centers of spinal sympathetic and parasympathetic nuclear regions or to the peripheral autonomic ganglia and nerves.

Electric stimulation devices, as described in e.g. US 2006/0190047 A1, are known in the field of micturition disorders, i.e. disorders of the urine-passing and bladder system. Such stimulation devices have, until now, already been used for micturition disorders of other types. By contrast, only medicinal therapies or much more invasive measures are offered to patients with paraplegia and neurogenic disturbances of micturition. However, the minimally invasive implantation thereof is advantageous.

Spinal paraplegia, a synonym for paraplegia, paraplegic lesions, transversal syndrome, is understood to mean a group of symptoms that occur if the nerve lines in the spinal cord are interrupted. The cause can be injury to the spinal cord, e.g. in the case of vertebral fractures, or else tumors and other specific diseases, e.g. multiple sclerosis. Here there is neuronal dysfunction from the region of the damage, which may, e.g. in the region of the urogenital tract, lead to incontinence/problems when passing urine, detrusor sphincter dyssynergia (DSD) and to a loss of sexual functions and bowel movements (dysfunction of the lesser pelvis).

The most difficult event, DSD, leads to impaired coordination of the musculature required for a normal bladder function with the formation of residual urine and increased intravesical pressure during micturition. This can lead to detrusor damage, vesicoureteral reflux and, ultimately, to kidney damage as a result thereof.

Moreover, the sexual functionality may also be greatly impaired in the case of paraplegia, particularly in the case of male patients due to the inability of having an erection.

Previous minimally-invasive therapies utilize stimulation electrodes, which are implanted at suitable positions, and support/take over the required stimulation of the neuronal structures. Here, the implantation is matched individually to the most successful stimulation result, which in turn significantly depends on the position of the electrode in respect of the musculature to be stimulated.

A problem here is that the position of the electrodes may shift at a later time because there is a movement of the body and the tissue that holds the electrode. The precise and matched positioning is lost in the process.

SUMMARY OF THE INVENTION

An object of the invention is to make available a device for positioning and keeping the position of stimulation electrodes, and also a method for uniformly programming and controlling the stimulation electrodes and for maintaining the micturition ability of patients with paraplegia, particularly with detrusor sphincter dyssynergia, and thus for generating complete continence in the case of normal urodynamic capacity.

The invention also relates to stool-regulating effects, i.e., influencing the function of the large intestine.

BRIEF DESCRIPTION OF THE DRAWINGS

For closer inspection of the present invention, the description of the invention contains a reference to the respective reference signs of the exemplary embodiment illustrated in the figures.

DETAILED DESCRIPTION OF THE INVENTION

Figure 1:
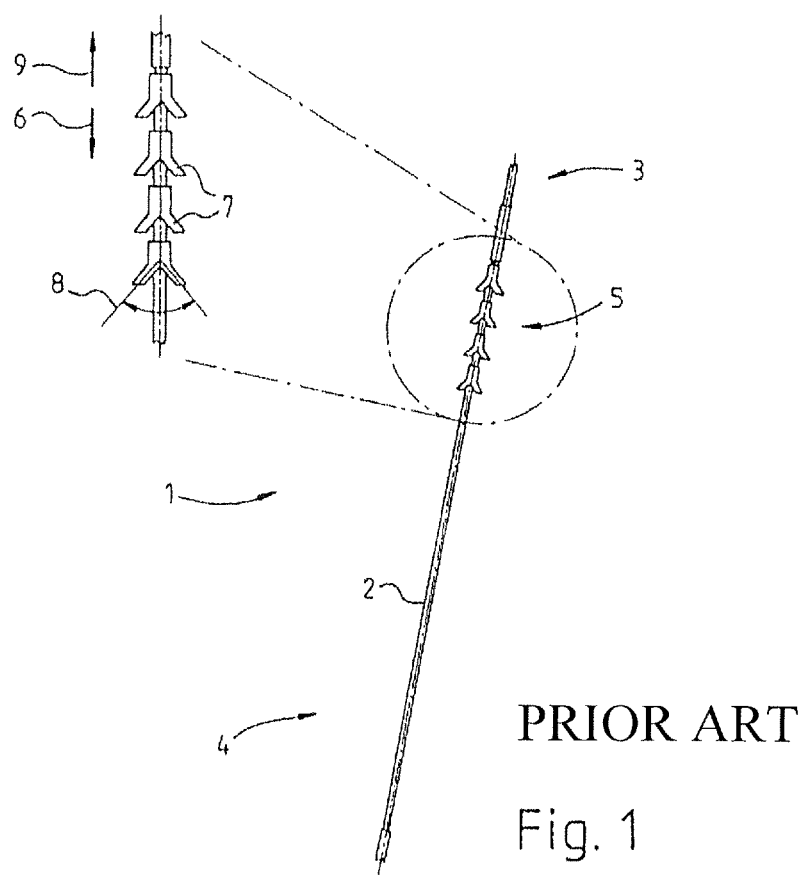
FIG. 1 shows a stimulation electrode according to the prior art.
Figure 2:
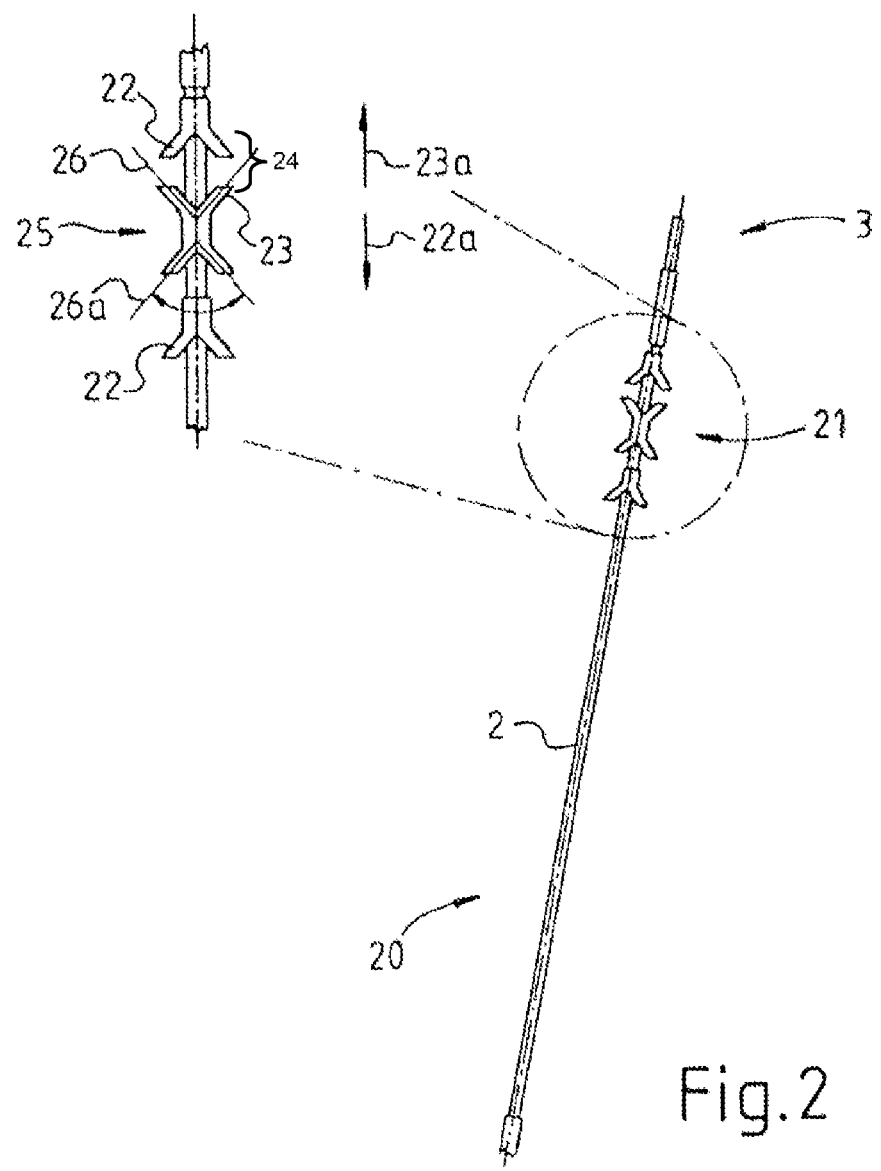
FIG. 2 shows a stimulation electrode according to the invention.
Figure 3:
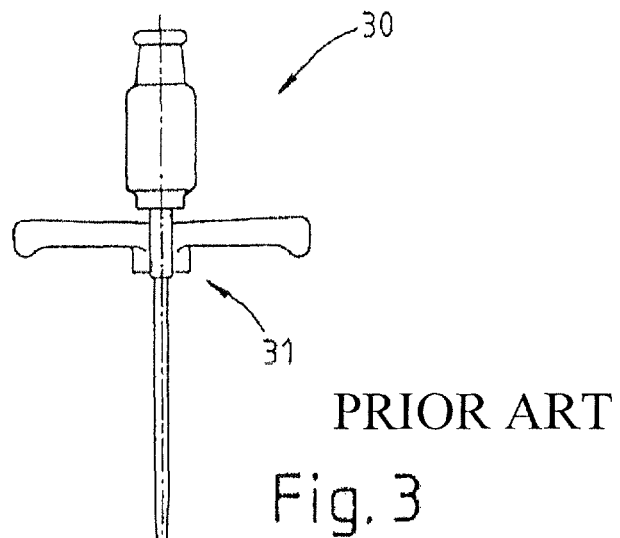
FIG. 3 shows an insertion aid according to the prior art.
Figure 4:
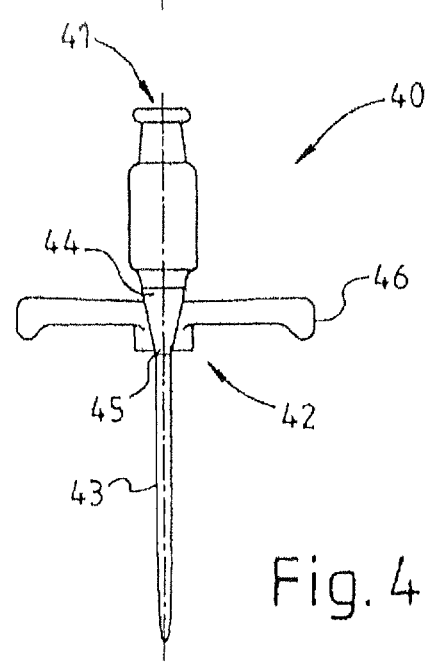
FIG. 4 shows an insertion aid according to the invention.

According to the invention, the stimulation electrode (20) is embodied for a stimulation device for stimulating organs in the case of spinal paraplegia, more particularly in the case of detrusor sphincter dyssynergia and dysfunctions of organs in the lesser pelvis, comprising an electrode shaft (2), at one end of which an electrode tip (3) is arranged for emitting a stimulation signal and at the other end of which a connection region (4) is provided for a signal line. In this case, the fixation should be arranged on the electrode in the vicinity of the electrode points in order that—even in the case of patients with paraplegia who break down muscular tissue and subcutaneous fatty tissue at this localization—better fixation and orientation is possible with respect to the nerve root to be stimulated (approximately ⅓ less than the conventional distance between proximal electrode and distal hook). It furthermore comprises at least one fixing means (5, 21) for fixing the position of the electrode shaft (2) in the surrounding tissue along the longitudinal axis of said electrode shaft, this being characterized in that the fixing means (21) is embodied respectively having at least one holding means (22, 23) preventing a withdrawal in the withdrawal direction (22a) and an advance in the advance direction (23a).

This ensures that the exact position is maintained. In the prior art, it is only the withdrawal direction (6) that is secured by holding means (7) with a hook angle (8). The advance direction (9) does not experience any barbed hooks.

One development lies in a stimulation electrode (20), characterized in that the holding means (22) preventing the withdrawal and holding means (23) preventing the advance are spaced apart by a clamping region (24) and connected thereto, the clamping region (24) establishing a force-fit connection between electrode shaft (2) and the holding means (22, 23).

In a further embodiment of the stimulation electrode, provision is made for a kink region (25) on the connection between clamping region (24) and holding means (22, 23), preferably for a constriction for pivoting the holding means if a threshold force is exceeded.

As a result of this, the electrode can be withdrawn despite the holding means present if a sufficient pulling force is applied. In this case, the holding means fold over and only still constitute a very much reduced resistance against movement.

In a further form of the stimulation electrode, the latter is characterized in that the holding means (22, 23) are formed by barbed hooks directed away from the electrode shaft (2) at a hook angle (26, 26a).

One embodiment of the stimulation electrode provides for the holding means (22) preventing a withdrawal to be designed symmetrically to a mirror plane intersecting the electrode shaft (2) perpendicularly, with respect to the holding means (23) preventing an advance.

This achieves a comparable holding effect in both advance directions (22a, 23a).

A further embodiment of the stimulation electrode includes the fact that the holding means (22, 23) are formed by expanding elements that taper toward the electrode shaft at an opening angle (26, 26a), the tip of the angle being directed counter to the respective movement direction (22a, 23a) in which the holding means (22, 23) prevents the advance.

Furthermore, the invention comprises an "insertion aid" (40), i.e. an insertion aid for a stimulation electrode (20) according to the invention, which insertion aid comprises an electrode entrance (41) for introducing the electrode shaft (2) into the insertion aid (40), a guide (42) for inactivating the holding means (22, 23) during the positioning procedure of the electrode (20) and a cannula (43) for penetrating tissue and is characterized in that the guide (42) has a conical design.

As a result of the conical guide, the holding means are placed against the electrode shaft and introduced into the cannula. The holding means can re-assume e.g. their hook angle (26, 26a) only after leaving the cannula and thus provide the desired hold in the tissue.

In one development, the insertion aid according to the invention is characterized in that the conical guide is arranged such that a widened opening region (44) is on the side of the electrode entrance (41) and a smaller opening region (45) compared thereto is on the side of the cannula (43).

Advantageously, provision is made for a handling aid (46) on the insertion aid.

An insertion aid (30) according to the prior art only has a cylindrical, rectilinear guide region (31) which cannot, in particular, exert any influence on holding means preventing an advance. These could not be applied using the insertion aid (30) according to the prior art.

Furthermore, the invention relates to a method for stimulating organs in the case of spinal paraplegia, more particularly in the case of detrusor sphincter dyssynergia, by means of preferably 2 or 4 stimulation electrodes according to the invention, the method comprising the following steps.

A soft start of the stimulation is carried out over a first short period of time—the "start time"—in a first method step.

Alternate switching on for an "on time" and subsequent switching off for an "off time" of the stimulation take place in a second method step, the intensity of the stimulation signal during the second method step and also the ratio of "on time" to "off time" being available as selectable program parameters.

The method according to the invention provides the "start time" in the range of 1 s-30 s for selection as a parameter, preferably as 8 s.

A further preferred parameter of the method comprises that the "on time" in a first program lies in the range of 10 min-60 min, and preferably is 29 min.

A further moreover preferred parameter of the method comprises that the "off time" lies in the range of 5 min-40 min, and preferably is 15 min.

In a further embodiment of the method, the "on time" in a second program lies in the range of 1 min-30 min and a stimulation signal is continuously between 0.5 V and 3 V, preferably 0.7 V, in the process. By way of example, this embodiment serves to initiate an erection. Moreover, programming in respect of initiating micturition can be carried out under co-stimulation with the detrusor stimulation if the sacral neuromodulation is implanted at an early stage.

Figures 5A, 5B:
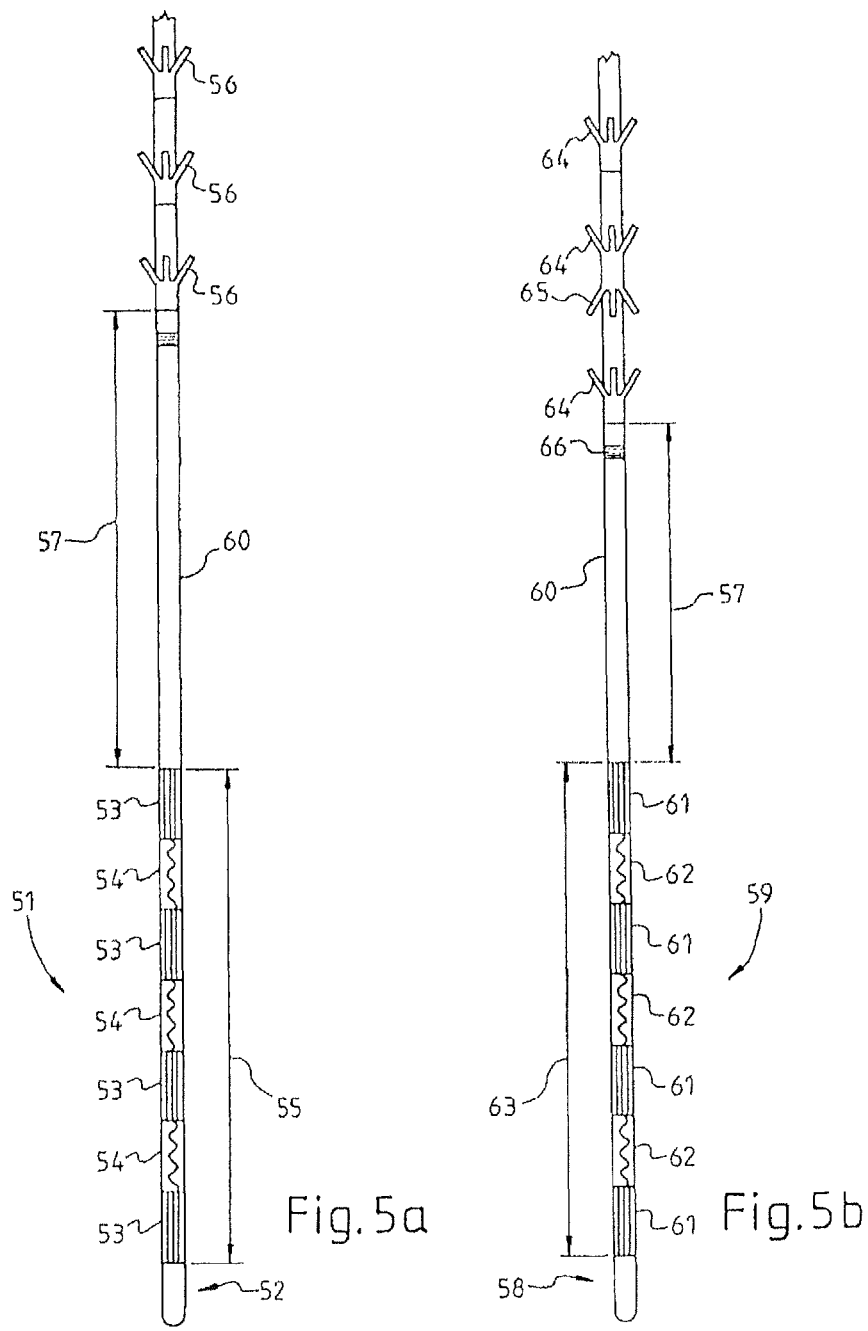
FIG. 5a shows an electrode according to the prior art.
FIG. 5b shows an electrode according to the invention.

A further expedient embodiment of the stimulation electrode according to the invention is illustrated in FIGS. 5a and 5b. FIG. 5a shows an electrode according to the prior art. The electrode tip 51 comprises a front tip end 52, which simplifies the penetration into the tissue. Following the tip end, contact regions 53 (electrode rings) are arranged on the electrode shaft and separated from one another by insulation regions 54. This forms a stimulation region 55 with a plurality of electrode rings 53 on the electrode tip 51 and said region can come into direct contact with the nerve(s).

Following the stimulation region 55, an arrangement of barbed hooks 56, which are used as withdrawal-preventing holding means, follow at a distance 57 of approximately 8 mm.

FIG. 5b shows a stimulation electrode according to the invention with a front tip end 58 at the electrode tip 59, following which electrode rings 61 are arranged on the electrode shaft 60 at a distance of approximately 3 mm. The electrode rings 61 themselves are spaced apart from one another by intermediate regions 62, the distance in each case likewise being approximately 3 mm. Stimulation of the nerve(s) occurs in this stimulation region 63 of the arrangement of the electrode rings 61.

The stimulation region 63 is offset from the region of the fixing means with the holding means 64 preventing a withdrawal (barbed hooks in the pulling direction) and holding means 65 preventing an advance (barbed hooks in the pushing direction) by a distance of approximately 4-6 mm, preferably 5 mm, along the electrode shaft 60. The closer positioning of the fixing means achieves improved positional stability of the implanted stimulation electrode and hence an improved working result. Additionally, one or more markings 66 are also provided on the electrode shaft; these mark the penetration depth, particularly during the application procedure of the electrode.

In one preferred embodiment, the method according to the invention is distinguished by virtue of the fact that, during a first program, stimulation of a is effected a range of between 0.5 V and 3 V, preferably at 0.7 V.

Additionally, if the second program is initiated on its own (optionally erection), it can act as preparation for some purpose and can achieve a desired effect if switched on at the same time as program 1 of a second stimulator. Thus, an improved result can be achieved, optionally, for initiating micturition by pre-stimulation with the second program and adding the basic program (programming 1). The second program can also operate in a range of between 0.5 V and 3 V, preferably at 0.7 V.

However, the subject matter of the invention is not restricted to the exemplary embodiments but rather comprises all those embodiments that make use of the concept that is essential to the invention.

LIST OF REFERENCE SIGNS

1 Electrode (prior art)
2 Electrode shaft

3 Electrode tip
4 Connection region
5 Fixing means
6 Withdrawal direction
7 Holding means preventing a withdrawal
8 Hook angle
9 Advance direction
20 Electrode
21 Fixing means
22 Holding means preventing a withdrawal
22a Withdrawal direction
23 Holding means preventing an advance
23a Advance direction
24 Clamping region
25 Kink region
26 Hook angle (advance)
26a Hook angle (withdrawal)
30 Insertion aid (prior art)
31 Guide
40 Insertion aid
41 Electrode entrance
42 Guide
43 Cannula
44 Widened opening region
45 Reduced opening region
46 Handling aid
51 Electrode tip
52 Front tip end
53 Contact region
54 Insulation region
55 Stimulation region
56 Barbed hook
57 Distance
58 Tip end
59 Electrode tip
60 Electrode shaft
61 Electrode rings
62 Intermediate region
63 Stimulation region
64 Barbed hook in the pulling direction
65 Barbed hook in the pushing direction
66 Marking

What is claimed:

1. A stimulation electrode for a stimulation device for stimulating organs in the case of spinal paraplegia, comprising:
an electrode shaft, at one end of which an electrode tip is arranged for emitting a stimulation signal and at the other end of which a connection region is provided for a signal line, and at least one fixing mechanism for fixing the position of the electrode shaft in the surrounding tissue of a subject along the longitudinal axis of said electrode shaft, wherein the fixing mechanism has at least one holding member to prevent a withdrawal and at least one holding member to prevent an advance relative to the surrounding tissue,
wherein the holding members for preventing the withdrawal and the advance are spaced apart by a clamping region and connected thereto, the clamping region establishing a force-fit connection between the electrode shaft and the holding members,
wherein a kink region is provided on the connection between the clamping region and the holding members to define a constriction for pivoting the holding members if a threshold force is exceeded, and
wherein on the electrode tip between a front tip end and a region of the fixing mechanism, electrode rings are provided for contact with nerves, the electrode rings having at least one of a length and a distance from one another of approximately 2.5 mm to 3.5 mm and a distance of 4 mm to 6 mm being provided between the fixing mechanism and the electrode rings.

2. The stimulation electrode as claimed in claim 1, wherein the holding members are formed by barbed hooks directed away from the electrode shaft at a hook angle.

3. The stimulation electrode as claimed in claim 1, wherein the holding member for preventing a withdrawal is designed symmetrically to a mirror plane intersecting the electrode shaft perpendicularly, with respect to the holding member for preventing an advance.

4. The stimulation electrode as claimed in claim 1, wherein the holding members are formed by expanding elements that taper toward the electrode shaft at an opening angle, the tip of the angle being directed counter to the respective movement direction in which the holding member prevents the advance.

5. The stimulation electrode as claimed in claim 1, wherein the distance provided between the fixing mechanism and the electrode rings is 4 mm.

6. The stimulation electrode as claimed in claim 1, wherein the electrode rings have a length of approximately 3 mm and the distance from one another is approximately 2.5 to 3.5 mm.

7. An insertion aid for a stimulation electrode as claimed in claim 1, comprising
an electrode entrance for introducing the electrode shaft into the insertion aid,
a guide for inactivating the holding members during the positioning procedure of the electrode, and
a cannula for penetrating tissue,
wherein the guide has a conical design.

8. The insertion aid as claimed in claim 7, wherein the conical guide is arranged such that a widened opening region is on the side of the electrode entrance and a smaller opening region compared thereto is on the side of the cannula.

9. The insertion aid as claimed in claim 7, wherein a provision is made for a handling aid.

10. A method for stimulating organs in the case of spinal paraplegia using at least two stimulation electrodes as claimed in claim 1, wherein a soft start of the stimulation is carried out over a first period of time in a first step and alternate switching on for an "on time" and subsequent switching off for an "off time" of the stimulation take place in a second step, wherein the intensity of the stimulation signal during the second step and also the ratio of "on time" to "off time" are selectable program parameters.

11. The method as claimed in claim 10, wherein the first period of time is in the range of 1 to 30 seconds.

12. The method of claim 11, wherein the first period of time is 8 seconds.

13. The method as claimed in claim 10, wherein the "on time" in a first program is in the range of 10 to 60 minutes.

14. The method of claim 13, wherein the "on time" is 29 minutes.

15. The method as claimed in claim 10, wherein the "off time" is in the range of 5 to 40 minutes.

16. The method of claim 15, wherein the "off time" is 15 minutes.

17. The method as claimed in claim 10, wherein the "on time" in a second program is in the range of 1 to 30 minutes and a stimulation signal is continuously between 2 V and 4 V in the process.

18. The method of claim 10, wherein the spinal paraplegia is detrusor sphincter dyssynergia.

* * * * *